United States Patent
Ahn et al.

(10) Patent No.: US 12,303,589 B2
(45) Date of Patent: May 20, 2025

(54) COMPOSITION FOR HAIR REGENERATION COMPRISING MACROPHAGE-DERIVED EXTRACELLULAR VESICLE MIMETICS

(71) Applicant: KYUNGPOOK NATIONAL UNIVERSITY INDUSTRY-ACADEMIC COOPERATION FOUNDATION, Daegu (KR)

(72) Inventors: Byeong-Cheol Ahn, Daegu (KR); Prakash Gangadaran, Daegu (KR); Ramya Lakshmi Rajendran, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 229 days.

(21) Appl. No.: 17/713,257

(22) Filed: Apr. 5, 2022

(65) Prior Publication Data

US 2022/0323492 A1    Oct. 13, 2022

(30) Foreign Application Priority Data

Apr. 9, 2021    (KR) .................. 10-2021-0046286

(51) Int. Cl.
| | |
|---|---|
| A61K 35/15 | (2025.01) |
| A61K 8/98 | (2006.01) |
| A61P 17/14 | (2006.01) |
| A61Q 7/00 | (2006.01) |
| C12N 5/0786 | (2010.01) |

(52) U.S. Cl.
CPC .............. *A61K 8/983* (2013.01); *A61K 35/15* (2013.01); *A61P 17/14* (2018.01); *A61Q 7/00* (2013.01); *C12N 5/0645* (2013.01)

(58) Field of Classification Search
CPC ......... A61K 35/15; A61K 8/983; A61P 17/14; A61Q 7/00; C12N 5/0645
See application file for complete search history.

(56) References Cited

U.S. PATENT DOCUMENTS

2013/0209528 A1*   8/2013   Levi .................. A61K 8/981
                                                            424/520

FOREIGN PATENT DOCUMENTS

| KR | 20-2012-0007026 U | 10/2012 |
|---|---|---|
| KR | 10-2017-0044999 A | 4/2017 |
| KR | 10-1986044 B1 | 6/2019 |
| KR | 101986044 * | 6/2019 |

OTHER PUBLICATIONS

R.L. Rajendran, et al. "Macrophage-Derived Extracellular Vesicle Promotes Hair Growth," Cells 2020, 9, 856, pp. 1-20. (Year: 2020).*
S. Sil, et al. "Strategies for the use of Extracellular Vesicles for the Delivery of Therapeutics," J Neuroimmune Pharmacol (2020) 15: 422-442. (Year: 2020).*
R.L. Rajendran, et al. "Extracellular vesicles derived from MSCs activates dermal papilla cell in vitro and promotes hair follicle conversion from telogen to anagen in mice," Scientific Reports 17: 15560, 2017, 1-12. (Year: 2017).*
English Translation of KR101986044 from Google Patents (Year: 2024).*
S. C. Jang, et al. "Bioinspired Exosome-Mimetic Nanovesicles for Targeted Delivery of Chemotherapeutics to Malignant Tumors," ACSNANO, vol. 7, No. 9, 7698-7710 (2013). (Year: 2013).*
Jang Su Chul et al., "Bioinspired Exosome-Mimetic Nanovesicles for Targeted Delivery of Chemotherapeutics to Malignant Tumors", ACS NANO, vol. 7, No. 9, Sep. 4, 2013 (Sep. 4, 2013), pp. 7698-7710.
Cao Lei et al., "Neural progenitor cell-derived nanovesicles promote hair follicle growth via miR-100", Journal of Nanobiotechnology, vol. 19, No. 1, Jan. 11, 2021 (Jan. 11, 2021).
Gangadaran Prakash et al., "Extracellular Vesicle- and Extracellular Vesicle Mimetics-Based Drug Oelivery Systems: New Perspectives, Challenges, and Clinical Oevelopments", Pharmaceutics, vol. 12, No. 5, May 11, 2020 (May 11, 2020), p. 442.
Ramya Lakshmi Rajendran et al., "Macrophage-Derived Extracellular Vesicle Promotes Hair Growth", Cells 2020, 9(4), 856; https://doi.org/10.3390/cells9040856.

* cited by examiner

*Primary Examiner* — Michael P Cohen
(74) *Attorney, Agent, or Firm* — Revolution IP, PLLC

(57) ABSTRACT

The present invention relates to a composition for hair regeneration comprising a macrophage-derived extracellular vesicle mimetics, and since macrophage-derived extracellular vesicle mimetics are well absorbed into dermal papilla cells, have an excellent effect in promoting the proliferation of dermal papilla cells, as well as having an activity to increase the level of hair-induced proteins, it is excellent in the effects of proliferation of dermal papilla cells and hair increase and thus a composition comprising macrophage-derived extracellular vesicle mimetics can be provided for hair regeneration.

8 Claims, 7 Drawing Sheets

COMPOSITION FOR HAIR REGENERATION COMPRISING MACROPHAGE-DERIVED EXTRACELLULAR VESICLE MIMETICS

CROSS REFERENCE TO PRIOR APPLICATIONS

This application claims priority to Korean Patent Application No. 10-2021-0046286 filed on Apr. 9, 2021. The entire contents of the above-identified application are hereby incorporated by reference.

TECHNICAL FIELD

The present invention relates to a composition for hair regeneration comprising a macrophage-derived extracellular vesicle mimetics.

BACKGROUND ART

Hair loss is caused by falling out hair due to genetic or environmental factors, and genetic factors are considered the most important factor, but recently, hair loss due to acquired factors is increasing due to the increase in social stress and environmental pollution. Acquired factors include excessive stress or tension in the scalp muscles, excessive secretion of male hormones or female hormones, seborrheic dermatitis and atopic constitution, physical stimulation, excessive intake of fat and pollution, or insufficient supply of protein, vitamins, and hormones from the blood, or a decrease in blood circulation in the blood vessels at the root of the hair. In modern people, regardless of age or gender, the development of symptoms of hair loss, scalp inflammation, dandruff, oily hair, and dry hair is increasing from infants to the elderly due to acquired factors including many environmental and psychological factors such as imbalance in diet, pollutions of harmful air, polluted drinking water and acid rain, and drug abuse and stress.

In order to improve this hair loss, efforts are continuing around the world, and a plurality of blood circulation promoters, carotene solubilizers, bactericides, keratolytic agents, an agent for blood circulation promotion by local stimulation, an agent for hair follicle function enhancement, anti-male hormones, anti-seborrheic agents, amino acids and Vitamins and the like have been used in combination, but it has not been reported that they show a clear effect so far. In addition, in order to prevent hair loss of modern people as described above, artificial chemical agents are being developed for shampoos or detergents and drugs for hair loss prevention, but it is not only ineffective in preventing hair loss, but also weakens the skin and aggravates the symptoms of hair loss and hypotrichosis.

DISCLOSURE

Technical Problem

In order to solve the above problems, an object of the present invention is to produce a composition comprising macrophage-derived extracellular mimetics that exhibits an effective effect on the proliferation of dermal papilla cells and promotes hair growth for hair regeneration.

Technical Solution

The present invention provides a pharmaceutical composition for hair regeneration comprising macrophage-derived extracellular vesicle mimetics as an active ingredient.

In addition, the present invention provides a cosmetic composition for hair regeneration comprising macrophage-derived extracellular vesicle mimetics as an active ingredient.

In addition, the present invention provides a method of preparing a composition for hair regeneration comprising: (a) extruding macrophages sequentially using membrane filters of 10 μm, 5 μm, and 1 μm to prepare a solution containing extracellular vesicle mimetics; (b) centrifuging extruded solution in step (a) at 2,000 to 5,000 g for 5 to 30 minutes; and (c) recovering supernatant and centrifuging at 50,000 to 150,000 g for 30 to 90 minutes to separate extracellular vesicle mimetics.

Advantageous Effects

According to the present invention, because macrophage-derived extracellular vesicle mimetics are well absorbed into dermal papilla cells, have excellent effects in promoting proliferation of dermal papilla cells, and have an activity of increasing the level of hair-derived proteins, it is excellent in the effects of proliferation of dermal papilla cells and hair growth, and thus a composition comprising macrophage-derived extracellular vesicle mimetics can be provided for hair regeneration.

BEST MODE

Figure 1:
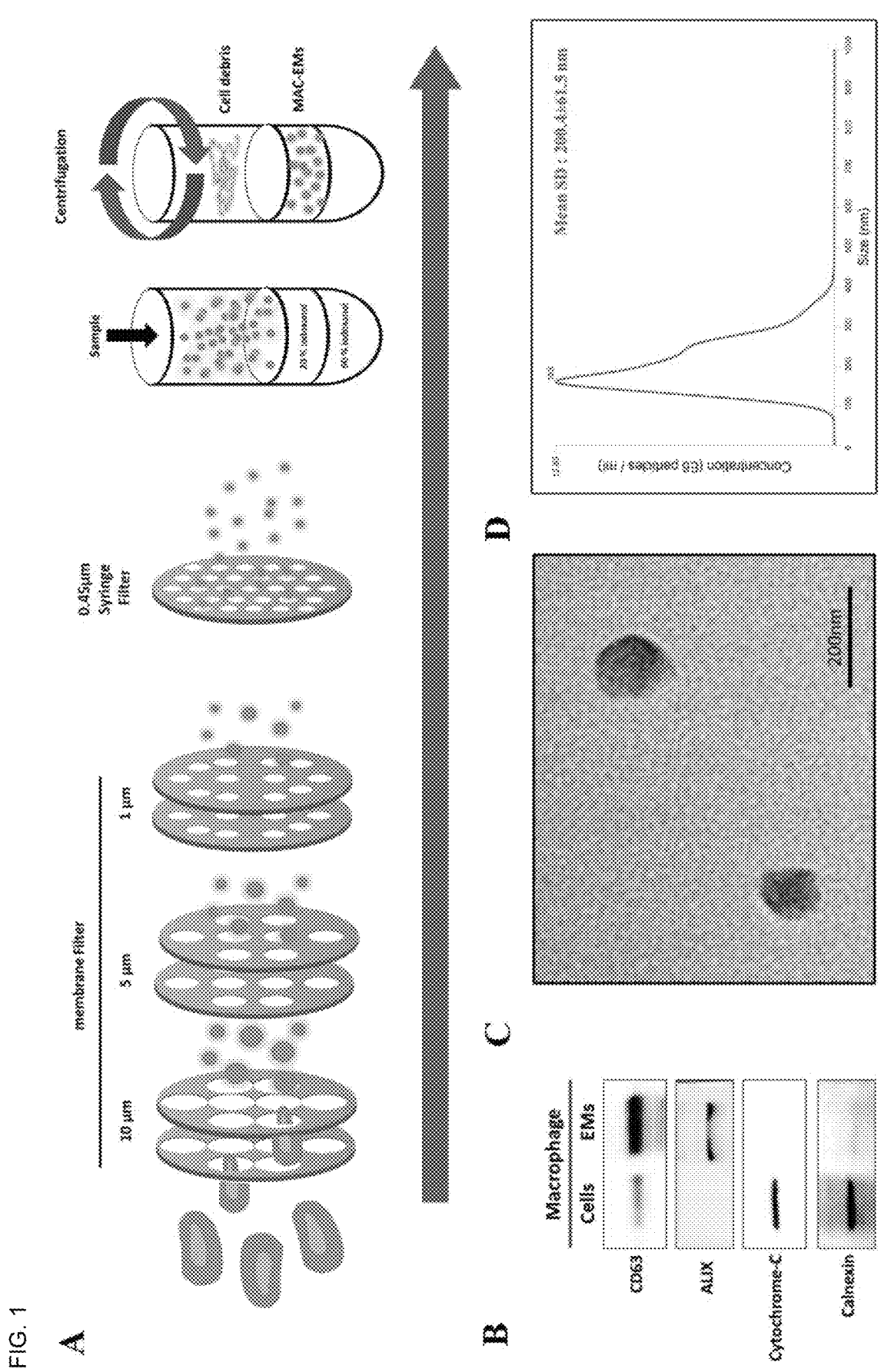
FIG. 1 shows the preparation method (A) and results of analyzing protein component (B), shape (C) and size (D) of the macrophage-derived extracellular vesicle mimetics prepared according to the present invention.

The terms used in this specification have been selected as currently widely used general terms as possible while considering the functions in the present invention, but these may vary depending on the intention of a person skilled in the art, or precedents, the emergence of new technology, and the like. In addition, in a specific case, there is a term arbitrarily selected by the applicant, and in this case, the meaning will be described in corresponding detail in the description of the invention. Therefore, the term used in the present invention should be defined based on the meaning of the term and the overall content of the present invention, rather than the name of a simple term.

Unless defined otherwise, all terms used herein, including technical or scientific terms, have the same meaning as commonly understood by one of ordinary skill in the art to which this invention belongs. Terms such as those defined in a commonly used dictionary should be interpreted as having a meaning consistent with the meaning in the context of the related art, and should not be interpreted in an ideal or excessively formal meaning unless explicitly defined in the present application.

Numerical ranges include the values defined in that range. Every maximum numerical limitation given throughout this specification includes all lower numerical limitations as if the lower numerical limitation were expressly written. Every minimum numerical limitation given throughout this specification includes all higher numerical limitations as if the higher numerical limitation were expressly written. All numerical limitations given throughout this specification will include all numerical ranges that are better within the broader numerical limits, as if the narrower numerical limitations were expressly written.

Hereinafter, the present invention will be described in detail.

The present invention provides a pharmaceutical composition for hair regeneration comprising macrophage-derived extracellular vesicle mimetics as an active ingredient.

The extracellular vesicle mimetics are a vesicle artificially prepared by extruding macrophages with a filter, and is distinguished from exosomes that are naturally secreted out of the cell due to fusion of the multivesicular bodies with the plasma membrane.

The extracellular vesicle mimetics may have a size of 100 nm to 300 nm, specifically, a size of 135.51 nm to 261.5 nm.

The extracellular vesicle mimetics may have a membrane-bound protein, CD63.

The extracellular vesicle mimetics can increase the levels of β-catenin, VRCN (Versican) and ALP, and increase the levels of phosphorylated AKT (pAKT) and phosphorylated ERK (pERK), and may increase the levels of Bcl-2 and PCNA, in dermal papilla cells.

The dermal papilla cells are cells present at the base of the hair follicle, and are responsible for hair growth and hair follicle cycle regulation by supplying oxygen and nutrients to the cells constituting the hair follicle. Therefore, when the proliferation of dermal papilla cells is promoted, hair becomes healthy, hair growth is promoted, and hair loss can be prevented. Because hair growth proceeds as the epithelial cells surrounding the dermal papilla divide to form a hair shaft, the dermal papilla cells play an important role in regulating the division of epithelial cells.

The extracellular vesicle mimetics can be absorbed into the dermal papilla cells to promote cell proliferation.

The extracellular vesicle mimetics may contain a drug for hair regeneration, for example, the drug for hair regeneration may be minoxidil, but it is not limited thereto.

In the present invention, the content of the additive included in the pharmaceutical composition is not particularly limited and may be appropriately adjusted within the content range used for conventional formulation.

The pharmaceutical composition may be formulated in the form of one or more agents selected from the group consisting of injectable preparations such as an aqueous solution, a suspension, an emulsion and external preparations such as a pill, a capsule, a granule, a tablet, a cream, a gel, a patch, a spray, an ointment, a plaster, a lotion, a liniment, a paste, and a cataplasma.

The pharmaceutical composition of the present invention may further include a pharmaceutically acceptable carrier and diluent for formulation. The pharmaceutically acceptable carriers and diluents include starch, sugar, and excipients such as mannitol, fillers and extenders such as calcium phosphate, cellulose derivatives such as carboxymethylcellulose, hydroxypropylcellulose, etc., and binders such as gelatin, alginate, and polyvinyl pyrrolidone, lubricants such as talc, calcium stearate, hydrogenated castor oil and polyethylene glycol, disintegrants such as povidone and crospovidone, surfactants such as polysorbates, cetyl alcohol, but they are not limited thereto. The pharmaceutically acceptable carrier and diluent may be biologically and physiologically compatible with the subject. Examples of diluents include saline, aqueous buffers, solvents, and/or dispersion media, but they are not limited thereto.

The pharmaceutical composition of the present invention may be administered orally or parenterally (e.g., intravenously, subcutaneously, intraperitoneally or topically) according to a desired method. For oral administration, it may be formulated as tablets, troches, lozenges, aqueous suspensions, oily suspensions, prepared powders, granules, emulsions, hard capsules, soft capsules, syrups or elixirs, and the like. For parenteral administration, it may be formulated as an injection, suppository, powder for respiratory inhalation, aerosol for spray, ointment, powder for application, oil, cream, etc.

The dosage of the pharmaceutical composition of the present invention depends on the patient's condition and weight, age, sex, health condition, dietary constitution specificity, the nature of the preparation, the degree of disease, the administration time of the composition, administration method, administration period or interval, excretion rate, and the drug form, and may be appropriately selected by those skilled in the art. For example, it may be in the range of about 0.1 to 10,000 mg/kg, but it is not limited thereto, and may be administered in divided doses from once to several times a day.

The pharmaceutical composition may be administered orally or parenterally (e.g., intravenously, subcutaneously, intraperitoneally or topically) according to a desired method. The pharmaceutically effective amount and effective dosage of the pharmaceutical composition of the present invention may vary depending on the formulation method, administration method, administration time and/or route of administration of the pharmaceutical composition, and a person of ordinary skill in the art can readily determine and prescribe an effective dosage for a desired treatment. Administration of the pharmaceutical composition of the present invention may be administered once a day, and may be administered several times.

In addition, the present invention provides a cosmetic composition for hair regeneration comprising macrophage-derived extracellular vesicle mimetics as an active ingredient.

The cosmetic composition may be formulated in one or more selected from the group consisting of skins, lotions, creams, serums, emulsions, essences, powders, foundations, sprays, mask packs, sheet packs, sleeping packs, wash-off packs, and peel-off packs. The cosmetic composition may be formulated by a conventional method.

Specifically, the cosmetic composition can be prepared in general emulsified formulations and solubilized formulations. For example, it may be formulated in lotion such as a softening lotion or a nourishing lotion; emulsions such as facial lotions and body lotions; creams such as nourishing creams, moisturizing creams, and eye creams; essence; makeup ointment; spray; gel; pack; sunscreen; makeup base; foundations such as liquid type, solid type or spray type; powder; makeup removers such as cleansing cream, cleansing lotion, and cleansing oil; or cleaning agents such as a cleansing foam, soap, body wash, but it is not limited thereto. In addition, the cosmetic composition may be formulated in an external preparation for the skin such as an ointment, patch, gel, cream, or spray, but it is not limited thereto.

In the cosmetic composition, in addition to the essential components in each formulation, other components may be appropriately blended within the range that does not impair the purpose according to the present invention, depending on the type or purpose of use and the like of the formulation.

The cosmetic composition may include a conventionally acceptable carrier, for example, oil, water, surfactant, humectant, lower alcohol, thickener, chelating agent, colorant, preservative, fragrance, etc. may be appropriately formulated, but it is not limited thereto.

The acceptable carrier may vary depending on the formulation. For example, when formulated into an ointment, paste, cream or gel, animal oil, vegetable oil, wax, paraffin, starch, tragacanth, cellulose derivative, polyethylene glycol, silicone, bentonite, silica, talc, zinc oxide or extracts thereof may be used.

When the cosmetic composition is formulated as powder or spray, lactose, talc, silica, aluminum hydroxide, calcium silicate, polyamide powder, or extracts thereof may be used as a carrier component, and in the case of a spray, it may further contain a propellant such as chlorofluorohydrocarbon, propane, butane or dimethyl ether.

When the cosmetic composition is formulated as solution or emulsion, solvent, solubilizer, or emulsifier may be used as a carrier component, and for example, water, ethanol, isopropanol, ethyl carbonate, ethyl acetate, benzyl benzoate, propylene glycol, 1,3-butylglycol oil may be used, and in particular, cottonseed oil, peanut oil, corn oil, olive oil, castor oil and sesame oil, glycerol fatty esters, fatty acid esters of polyethylene glycol or sorbitan may be used.

When the cosmetic composition is formulated as suspension, a liquid diluent such as water, ethanol or propylene glycol, a suspending agent such as ethoxylated isostearyl alcohol, polyoxyethylene sorbitol ester and polyoxyethylene sorbitan ester; microcrystalline cellulose, aluminum metahydroxide, bentonite, agar or tragacanth and the like can be used as a carrier component.

When the cosmetic composition is formulated as a soap, alkali metal salts of fatty acids, fatty acid hemiester salts, fatty acid protein hydrolysates, isethionate, lanolin derivatives, aliphatic alcohols, vegetable oils, glycerol, sugars, etc. may be used as a carrier component.

The cosmetic composition may additionally contain a fatty substance, organic solvent, solubilizer, thickening agent, gelling agent, softening agent, antioxidant, suspending agent, stabilizing agent, foaming agent, fragrance, surfactant, water, ionic or nonionic emulsifier, filler, sequestering agent, chelating agent, preservative agent, blocking agent, wetting agent, essential oil, dye, pigment, hydrophilic or lipophilic activator, which are commonly used in the industry according to the quality or function of the final product or adjuvants commonly used in the field of cosmetology or dermatology, such as any other ingredients commonly used in cosmetics.

However, the adjuvant and its mixing ratio may be appropriately selected so as not to affect the desirable properties of the cosmetic composition according to the present invention.

In addition, the present invention provides a method of preparing a composition for hair regeneration comprising: (a) extruding macrophages sequentially using membrane filters of 10 μm, 5 μm, and 1 μm to prepare a solution containing extracellular vesicle mimetics; (b) centrifuging extruded solution in step (a) at 2,000 to 5,000 g for 5 to 30 minutes; and (c) recovering supernatant and centrifuging at 50,000 to 150,000 g for 30 to 90 minutes to separate extracellular vesicle mimetics.

It may include a process of mixing macrophages in a solution containing a drug for hair regeneration in step (a), and the drug for hair regeneration may be minoxidil.

In step b), the extracellular vesicle mimetics may be filtered through a 0.45 μm filter and then separated by centrifugation.

MODES FOR CARRYING OUT INVENTION

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

EXPERIMENTAL EXAMPLE

Experimental Material and Method

The following experimental examples are intended to provide experimental examples commonly applied to each example according to the present invention.

1. Cell Culture

Raw 264.7, a murine macrophage cell line, was purchased from the American Type Culture Collection (Manassas, VA, USA). Raw 264.7 cells were cultured in DMEM-high glucose (HyClone, Logan, UT, USA) containing 10% FBS (fetal bovine serum, Hyclone) and 1% penicillin-streptomycin (Gibco, Carlsbad, CA, USA) at 37° C. under 5% $CO_2$ condition.

2. Dermal papilla cell culture

Dermal papilla (DP) cells were collected from patients to be receiving hair transplantation and performed after obtaining informed consent from all patients in accordance with the principles of the Declaration of Helsinki (IRB No.: KNU-2018-0161). DP cells were cultured at 37° C. in a 100 mm dish with DMEM-low glucose supplemented with 10% FBS and 1% antibiotics.

3. Preparation of Macrophage-Derived Extracellular Vesicle Mimetics (MAC-EM)

The Raw 264.7 cell line was cultured in DMEM-high glucose (HyClone, Logan, UT, USA) containing 10% FBS and 1% penicillin-streptomycin. When the cultured cells were saturated, the macrophages were extruded using 10 μm, 5 μm, and 1 μm polycarbonate membrane filters (nucleopore track-etched membrane) sequentially using an Avanti Polar Lipids (AL, USA) extruder to prepare extracellular vesicle mimetics (EM). The extracellular vesicle mimetics were filtered through a 0.45 μm filter, followed by two centrifugations (3000g×10 min, 4000 g×20 min) sequentially and then by ultracentrifugation (100000×60 min). Finally, pure EM (Opti-prep density gradient medium 60%) was obtained by treatment with a density gradient ultracentrifuge and the protein was measured using a BCA kit (Thermo Scientific, Waltham, MA, USA).

4. Western Blot Analysis

Extracellular vesicle mimetics (EM) and cell lysates were treated with to radioimmunoprecipitation assay buffer (Thermo Fisher Scientific Waltham, Mass., USA) containing a protease inhibitor cocktail (Sigma-Aldrich, Burlington, Mass., USA). The same amount of protein was loaded using 10% SDS-PAGE, separated and transferred to a polyvinylidene difluoride (PVDF) membrane. The blot was irradiated with a primary antibody and a secondary antibody conjugated with horseradish peroxidase. Signals were detected using enhanced chemiluminescence (GE Healthcare, USA) according to the manufacturer's instructions. Blot images were prepared using Picasa3 (version 3.9.1.4.1; Google, CA, USA) and/or PowerPoint program (Microsoft, USA).

5. Transmission Electron Microscopy

The MAC-EM pellet was resuspended in 100 μL of 2% paraformaldehyde. Then, 10 μL EM pellets were attached to the EM grid in carbon-coated Formvar for 20 min. For washing, the grid was transferred to a drop of PBS (100 μL) using sterile forceps, treated with 50 μL of 1% glutaraldehyde, incubated at 25° C. to 30° C. for 5 minutes, and washed with distilled water for 2 minutes. Samples were stained with 2% uranyl acetate and then washed with distilled water for 2 minutes. The above steps were repeated 7 additional times. Samples were completely dried before observation with a HT 7700 transmission electron microscope (Hitachi, Tokyo, Japan) for EM imaging.

6. Nanoparticle Tracking Analysis (NTA)

MAC-EM size was determined by NTA (Nano Sight LM10, Malvern). To dilute the samples, MAC-EM was dissolved in 500 folds of milli-Q purified water. The sample was inserted into a completely bubble-free cavity. The measurements were compared to a threshold of 20 to 60 particles per field. All measurements were performed in triplicate.

7. MAC-EM Absorption Analysis

MAC-EM labeled with the fluorescent dye DiD (1,1'-dioctadecyl-3,3,3',3'-tetramethyl indodicarbocyanine, 4-chlorobenzenesulfonate salt) was incubated with DP cells in a $CO_2$ incubator for 4 hours. Samples were fixed with 4% paraformaldehyde for 10 min at room temperature and loaded with DAPI. Fluorescence images were taken using a high-sensitivity super-resolution confocal laser scanning microscope (LSM 800 with AiryScan, Zeiss, Oberkochen, Germany).

8. Cell Proliferation Assay

DP cells were seeded in a 96-well plate at 5000 cells per well, and then cultured for 24 hours in a 37° C. $CO_2$ incubator, and then MAC-EM at various concentrations was added. Then, 10 μL of Cell Counting Kit-8 reagent (Dojindo Laboratories, Kumamoto, Japan) was added to the cells and incubated for 2 hours. Cell proliferation was measured using an ELISA reader at 450 nm according to the manufacturers instructions.

9. RNA Extraction and RT-PCR

RNA isolation was performed using Triazole reagent, and RNA was converted into cDNA using a cDNA kit (ABI, USA) through conventional PCR. Electrophoresis was performed using a 1% agarose gel, PCR products were separated, and band intensity was observed under UV light.

10. Biodistribution and Localization of Intradermally Injected MAC-EM in C57BL/6 mice A 5.5-week-old C57BL/6 male mouse (Hamamatsu, Shizuoka, Japan) was purchased, and the experiment was performed according to the management guidelines set by Kyungpook National University. To determine the optimal time interval between MAC-EM administrations, mice were intradermally injected with DiD-labeled MAC-EMs (MSC-EVMs/DiD), MAC-EMs were allowed to stay, and after 6, 24, 48 and 72 hours, the fluorescence images were analyzed by an IVIS Lumina III In Vivo Imaging System (PerkinElmer). After 72 hours, organs (heart, lung, liver, kidney, stomach, spleen, intestine and skin) were excised, and signals were observed and quantified using IVIS Lumina III. The skin was treated with cryosection and stained with DAPI. DiD signals of hair follicles (HF) were imaged with a high-sensitivity super-resolution confocal laser scanning microscope (LSM 800 with AiryScan, Zeiss, Oberkochen, Germany).

11. In Vivo Experiments 5.5-week-old C57BL/6 male mice (Hamamatsu, Shizuoka, Japan) were purchased. Two days before the experiment, the mice were anesthetized and hairs on the dorsal surface of the head were removed using an electric razor. Animals were divided into three groups: a control group (PBS; n=6), a treatment group (MAC-EMs; n=6), and a minoxidil group (n=3). Treatment was performed by administering 50 μg of MAC-EM by intradermal injection. 50 μL of PBS was injected to the control group, and 50 μL of minoxidil to the minoxidil group was applied to the dorsal surface twice a week for 4 weeks. After treatment, the mice were sacrificed and the treated area of the dorsal skin was collected for hematoxylin and eosin staining. The thickness of the dermal dermis (n=3) was measured at least 6 times using the ZEN Lite microscope software (ZEN Lite 2.3, Carl Zeiss, Germany).

12. Organ Culture

Human hair follicles (HF) were cultured as above, and hair follicles from three volunteers were used. Thereafter, the hair follicles were treated with PBS and MAC-EMs (0.1, 0.5, or 1 μg/mL). Hair shaft elongation was measured on days 3 and 6. Macroscopic images were taken on day 6.

13. Statistical Analysis

All data were expressed as mean±standard deviation (SD). Data from both groups were statistically analyzed by Student t-test or one-way/two-way ANOVA using MS Office Excel (Microsoft, USA) or GraphPad Prism7 software version 7.04 (GraphPad Software, Inc., La Jolla, CA, USA). P value <0.05 was considered statistically significant.

Example 1

Characterization of MAC-EM

In order to prepare a macrophage-derived extracellular vesicle mimetics (hereinafter referred to as 'MAC-EM') and analyze its characteristics, as shown in FIG. 1A, MAC-EM was prepared by extruding Raw 264.7 cells, which are mouse macrophages, sequentially using 10 μm, 5 μm, and 1 μm polycarbonate membrane filters. The prepared MAC-EM was filtered through a 0.45 μm filter and purified by centrifugation to obtain pure MAC-EM. To analyze the characteristics of MAC-EM, the levels of the membrane-bound protein CD63 and the cytoplasmic protein ALIX were measured through Western blotting. As shown in FIG. 1B, CD63 and ALIX levels were measured at high levels in MAC-EM, and calnexin, a mitochondrial and endoplasmic reticulum marker protein, was observed in macrophages and MAC-EM.

In order to analyze the shape of the MAC-EM, as a result of analyzing the prepared MAC-EM by transmission electron microscopy (TEM), it was confirmed that the shape of the MAC-EM was round. To analyze the size of the manufactured MAC-EM, nanoparticle tracking analysis (NAT) was performed and as a result, the average diameter of the MAC-EM was 200±61.5 nm, and MAC-EM with a size of 163 nm was found to have the highest distribution. The above results demonstrate that MAC-EM was successfully prepared in macrophages.

Example 2

Internalization of MAC-EM in Dermal Papilla Cells

Figure 2:
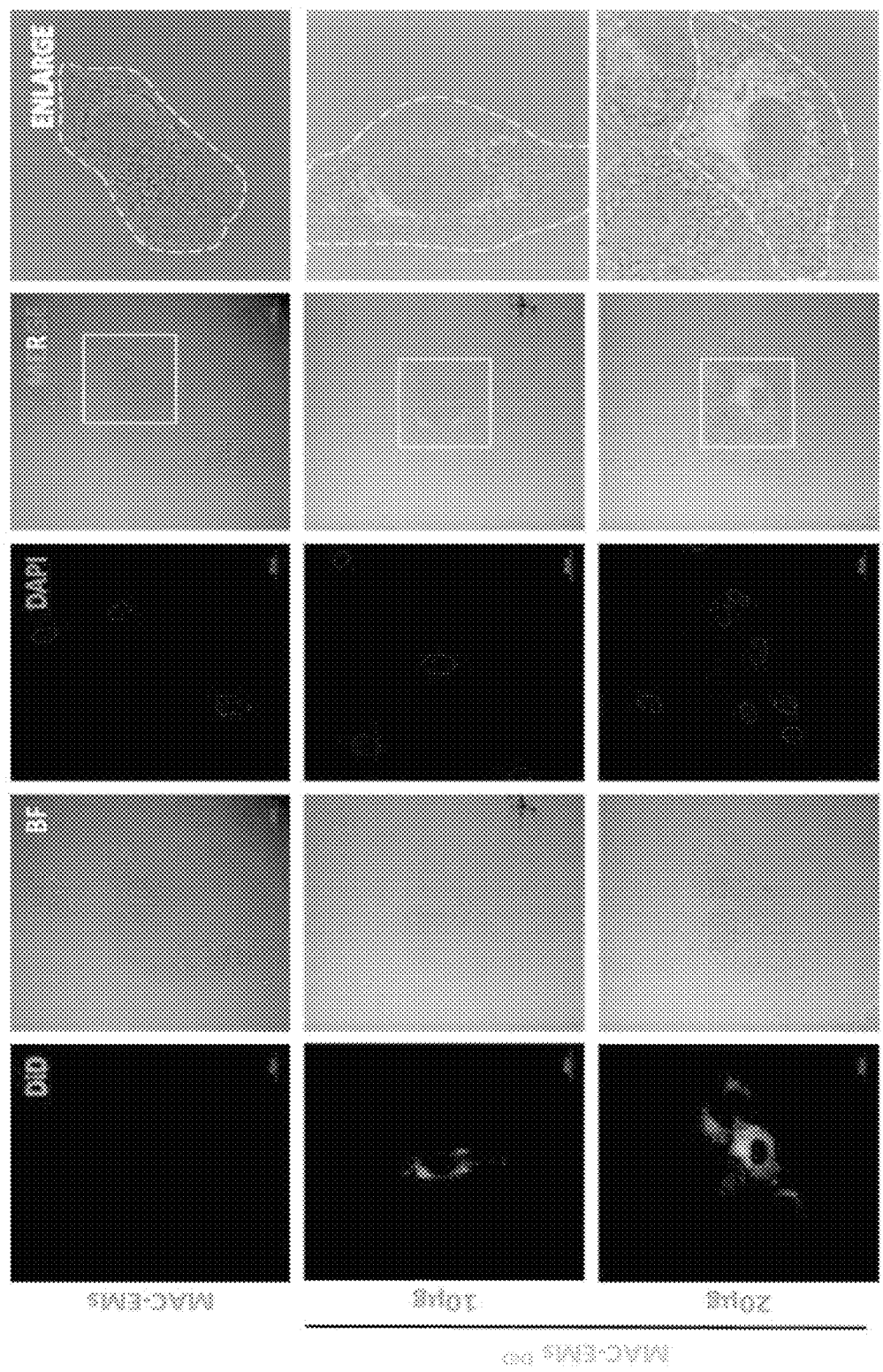
FIG. 2 shows a result of analysis with a fluorescence image to determine whether macrophage-derived extracellular vesicle mimetics prepared according to the present invention is absorbed into dermal papilla cells.

In order to confirm that the MAC-EM is absorbed and internalized into dermal papilla cells (hereinafter referred to as 'DP cells'), unlabeled MAC-EM (MAC-EM; 10 μg) or labeled MAC-EM (MAC-EM$^{DiD}$; 10 μg or 20 μg) was treated with DP cells and cultured for 1 hour to observe fluorescence images. As shown in FIG. 2, MAC-EM was found to interact closely around the DP cells, and it was confirmed that the MAC-EM was absorbed and internalized in the DP cells. The above results demonstrate that MAC-EM is well absorbed into dermal papilla cells.

Example 3

Effect of MAC-EM on Proliferation of DP Cells

Figure 3:
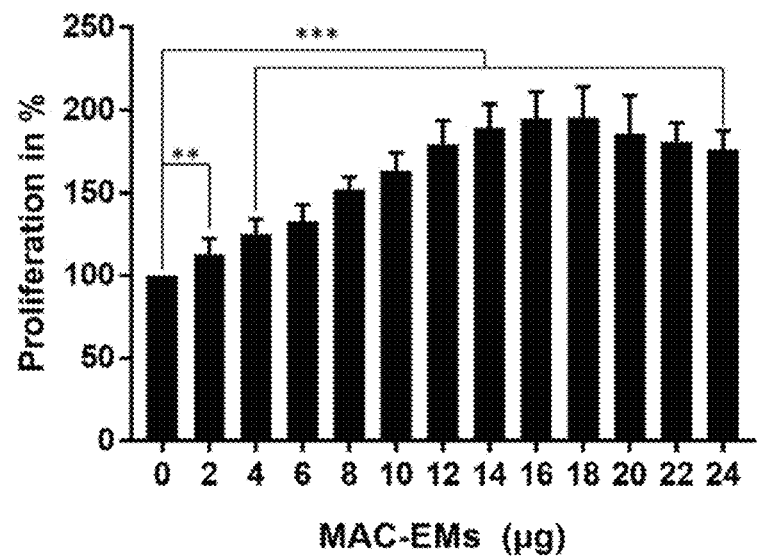
FIG. 3 shows a result of analyzing changes in cell proliferation of dermal papilla cells to determine whether macrophage-derived extracellular vesicle mimetics prepared according to the present invention affects the proliferation of dermal papilla cells.

In order to evaluate whether the MAC-EM affects the proliferation of DP cells, various concentrations of MAC-EM (2-24 μg) were applied to DP cells and the level of cell proliferation was evaluated. As shown in FIG. 3, when treated with MAC-EV, the proliferation of DP cells was significantly increased in a dose-dependent manner ($p<0.01$ and $p<0.001$). In particular, when MAC-EM of 14 μg to 20 μg was treated, the proliferation of DP cells was increased by about 2 times compared to the control group. The above results demonstrate that the treatment of MAC-EM is excellent in increasing the proliferation of DP cells.

Example 4

Effect of MAC-EM on Hair Induction and Proliferation Markers

Figure 4:
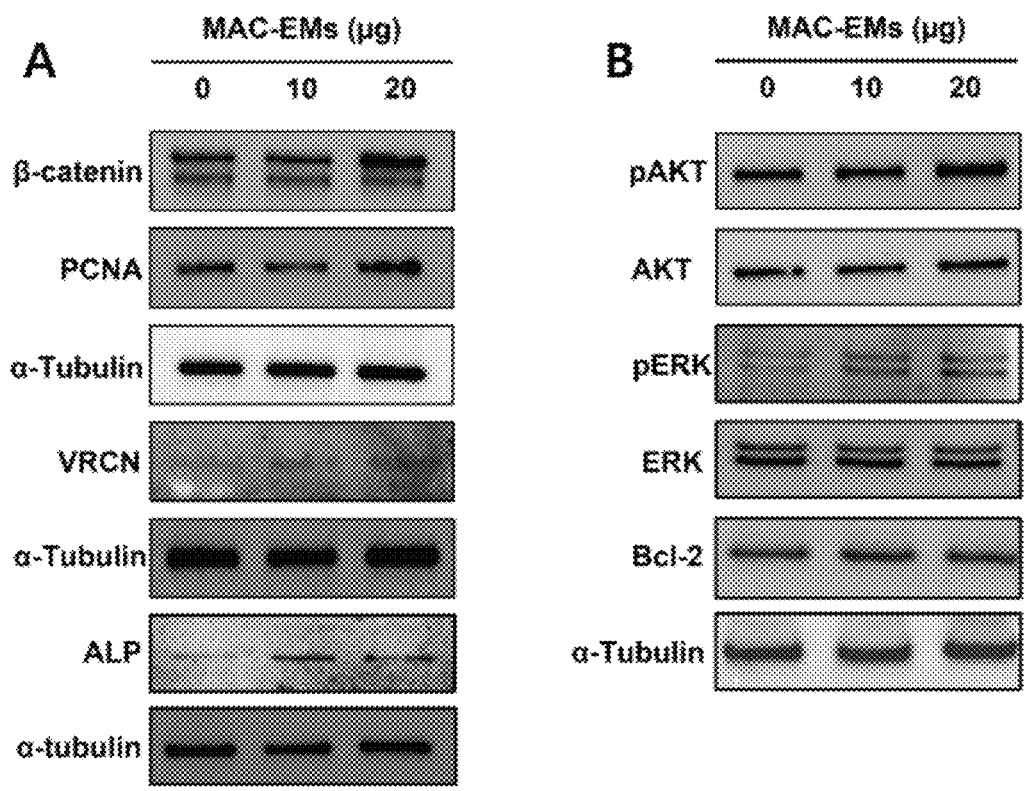
FIG. 4 shows a result of analyzing the effect of macrophage-derived extracellular vesicle mimetics prepared according to the present invention on the levels of hair flow protein (A) and proliferation marker (B).

In order to evaluate the effect of MAC-EM on hair induction activity in DP cells, MAC-EM was treated to DP cells and the levels of hair-inducing proteins β-catenin, VRCN (Versican) and ALP was investigated. As shown in FIG. 4A, it was found that the levels of three hair-inducing protein were increased compared to the control group according to the MAC-EM treatment dose. In addition, in order to evaluate the effect of MAC-EM on the proliferation of DP cells, MAC-EM was treated to DP cells and the level of proliferation markers was evaluated. As shown in FIG. 4B, when MAC-EM was treated, the levels of phosphorylated AKT (pAKT) and phosphorylated ERK (pERK) were increased compared to the control group. Similarly, the levels of Bcl-2 and PCNA, which are survival and proliferation markers, were also found to be increased when treated with MAC-EM compared to the control group.

Example 5

Effects of MAC-EM on Hair Growth Factors in DP Cells

Figure 5:
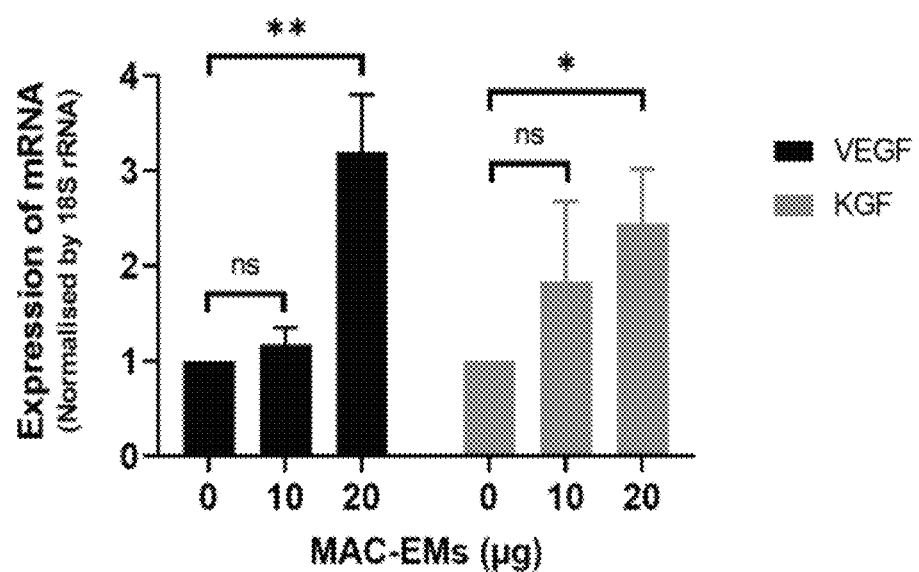
FIG. 5 shows a result of analyzing the effect of macrophage-derived extracellular vesicle mimetics prepared according to the present invention on hair growth factors.

To evaluate the effect of MAC-EM on hair growth factors in DP cells, DP cells were treated with MAC-EM, and mRNA expression of VEGF and KGF, hair growth factors, was measured. As shown in FIG. 5, mRNA expression of VEGF and KGF was found to increase with the treatment dose of MAC-EM compared to the control. When MAC-EM was treated with 10 μg and 20 μg, VEGF was shown to increase 1.17-fold and 3.19-fold, respectively, compared to the control group. When MAC-EM was treated with 10 μg and 20 μg, KGF was found to increase 1.84-fold and 2.44-fold, respectively, compared to the control group. The above results demonstrate that the expression of growth factor genes is increased by MAC-EM treatment.

Example 6

Maintenance of MAC-EM Treatment in C57BL/6 Mice

Figure 6:
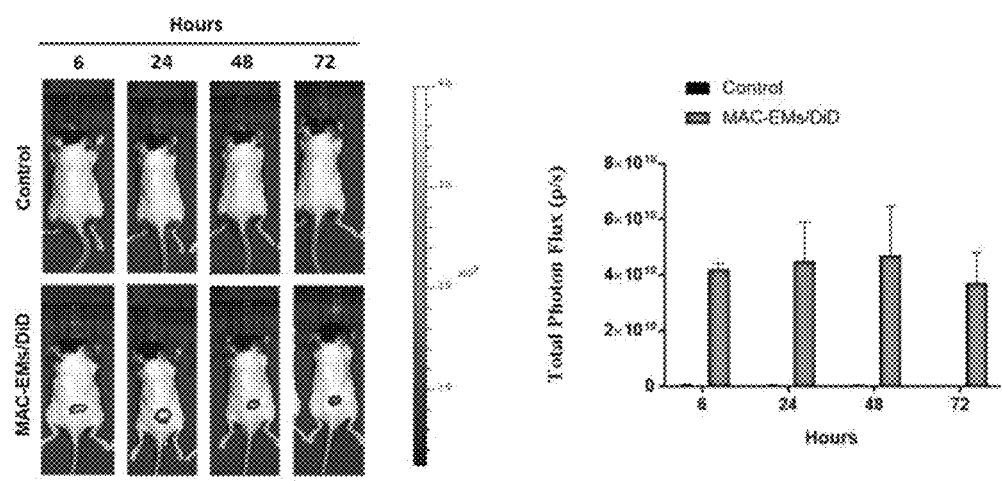
FIG. 6 shows a result of analyzing the location of the extracellular vesicle mimetics when the macrophage-derived extracellular vesicle mimetics prepared according to the present invention is administered to an animal model.
Figure 6:
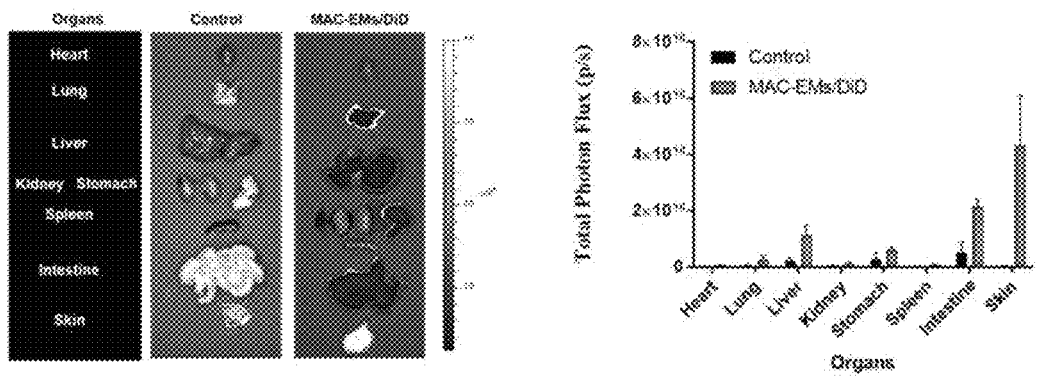
Figure 6:
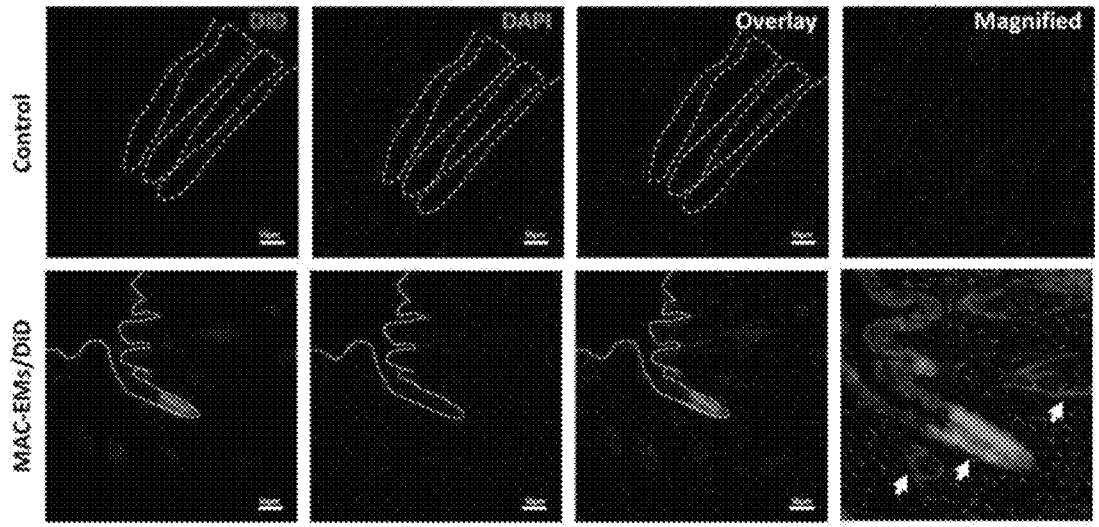

In order to evaluate whether the MAC-EM is maintained at the treatment site in the animal model, DiD-labeled MAC-EM was treated in a C57BL/6 mouse animal model, and the location of the MAC-EM was measured with a fluorescence image. The dorsal skin of C57BL/6 mice was shaved and imaging was performed at 6, 24, 48 and 72 hours after intradermal injection of MAC-EM$^{DiD}$. As shown in FIG. 6, the DiD signal was observed for 72 hours at the site of the intradermal injection through the imaging technique. In ex vivo images, the signal was strong in MAC-EM-injected skin and was weak in other organs such as lung, liver, stomach and intestine. Fluorescence imaging of skin tissue showed that most of the MAC-EM$^{DiD}$ signal was emitted from the hair follicles. The above results show that MAC-EM is maintained in the target binding site, skin hair follicles.

Example 7

Effect of MAC-EM Administration on Hair Follicles in C57BL/6 Mice

Figure 7:
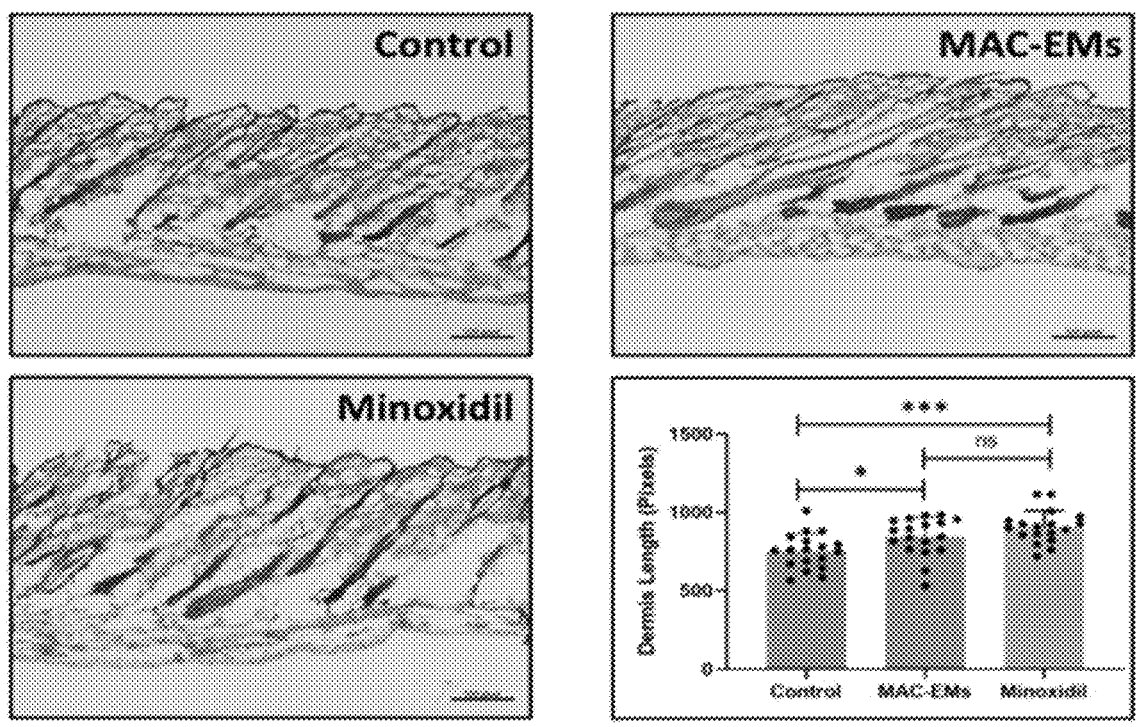
FIG. 7 shows a result of analyzing the effect of macrophage-derived extracellular vesicle mimetics on dermal regeneration when the macrophage-derived extracellular vesicle mimetics prepared according to the present invention is administered to an animal model.
Figure 7:
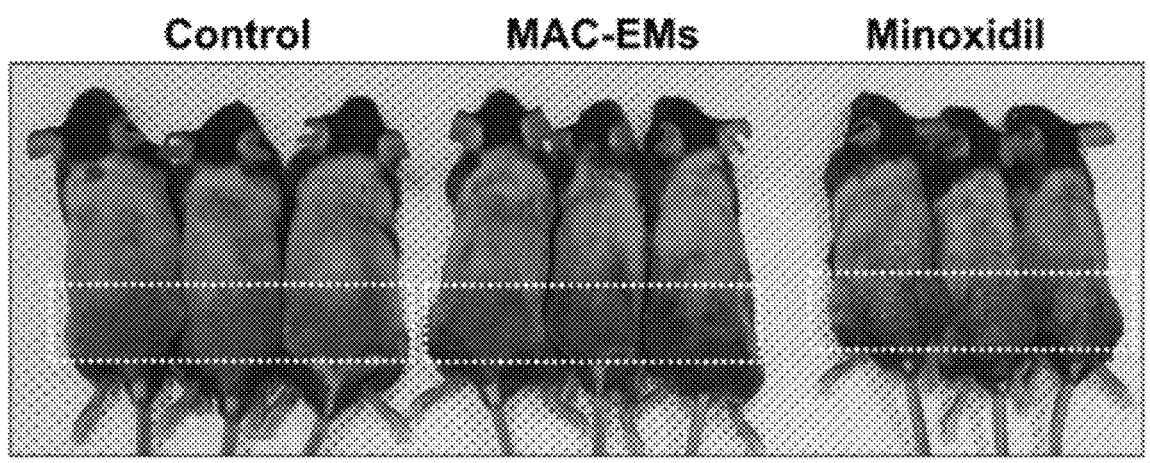

The effect of MAC-EM on hair regeneration in C57BL/6 mice was evaluated. As shown in FIG. 7, when MAC-EM was administered, hair regeneration was induced in C57BL/6 mice. The depth of the dermis is directly related to the transition from the anagen to the telogen in mice. As a result of measuring the length of the dermis of the histological part, the MAC-EM administration showed that the length of the dermis was significantly increased compared to the control group ($p<0.05$). In the minoxidil group, the length of the dermis was significantly increased compared to the control group, and there was no significant difference between the group administered with MAC-EM and the minoxidil group.

Figure 8:
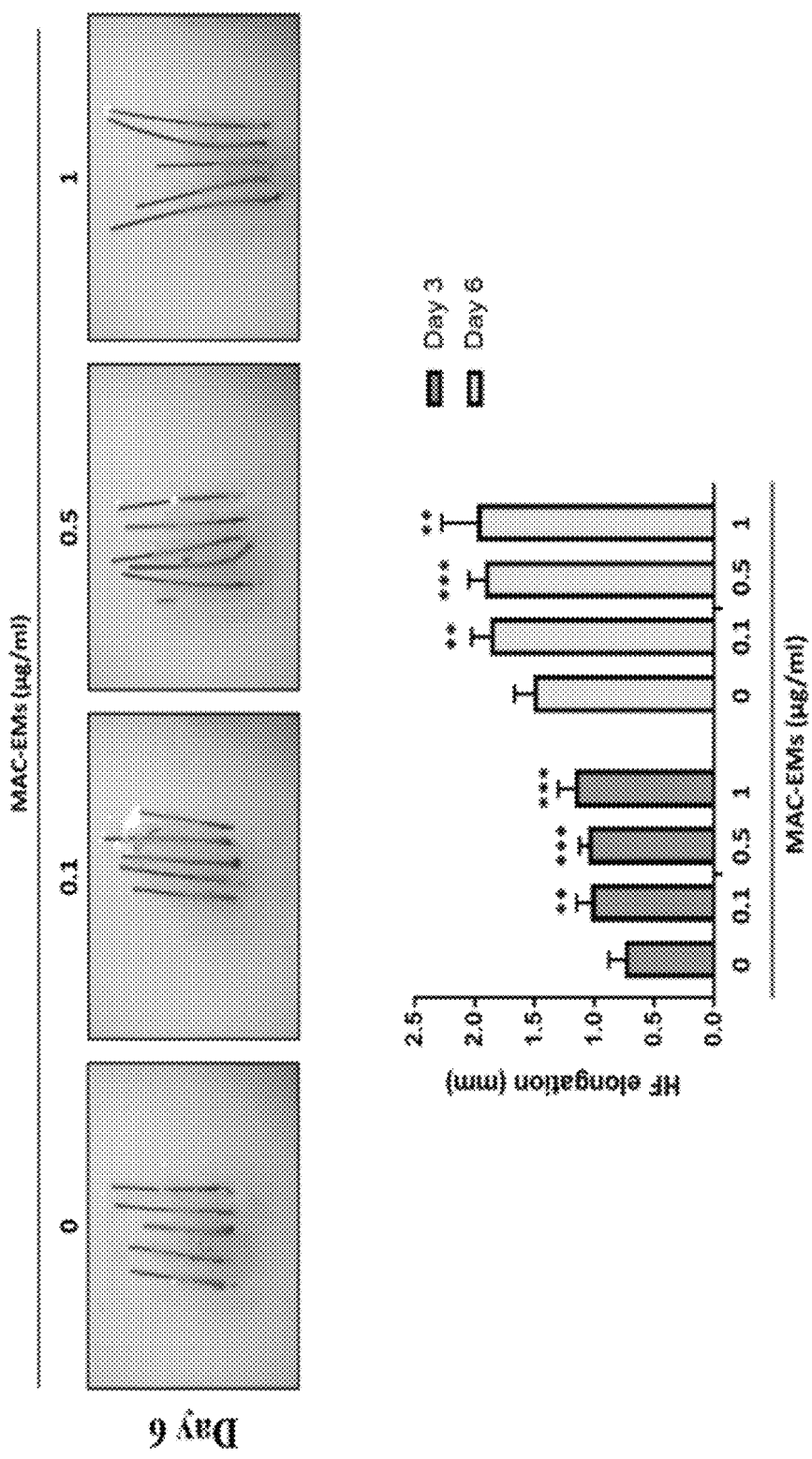
FIG. 8 shows a result of analyzing the effect of macrophage-derived extracellular vesicle mimetics on hair extension when the macrophage-derived extracellular vesicle mimetics prepared according to the present invention is administered to hair follicles of human scalp.

In addition, the effect of MAC-EM administration on hair growth was evaluated by measuring the hair shaft elongation of hair follicles in the human scalp by treatment with various concentrations of MAC-EM (0, 0.1, 0.5, and 1 µg/mL). As shown in FIG. 8, after 3 days of administration, hair shaft elongation was significantly increased compared to the control group ($p<0.01$ and $p<0.001$). In addition, after 6 days of administration, hair shaft elongation was significantly increased compared to the control group ($p<0.01$ and $p<0.001$). The above results demonstrate that MAC-EM administration can increase hair shaft growth in human hair follicles.

According to the present invention, since macrophage-derived extracellular vesicle mimetics are well absorbed into dermal papilla cells, have an excellent effect in promoting the proliferation of dermal papilla cells, as well as having an activity to increase the level of hair-induced proteins, it is excellent in the effects of proliferation of dermal papilla cells and hair increase and thus a composition comprising macrophage-derived extracellular vesicle mimetics can be provided for hair regeneration.

While the present invention has been particularly described with reference to specific embodiments and drawings thereof, it is apparent that this specific description is only a preferred embodiment and that the scope of the present invention is not limited thereby to those skilled in the art. That is, the practical scope of the present invention is defined by the appended claims and their equivalents.

What is claimed is:

1. A method of regenerating hair, comprising:
preparing macrophage-derived extracellular vesicle mimetics by extruding macrophages sequentially using polycarbonate membrane filters of 10 µm, 5 µm and 1 µm, wherein the macrophage-derived extracellular vesicle mimetics have a size of 163 nm, the macrophage-derived extracellular vesicle mimetics comprising calnexin; and
administering a pharmaceutical composition comprising the macrophage-derived extracellular vesicle mimetics as an active ingredient to a subject,
wherein the macrophage-derived extracellular vesicle mimetics are not naturally secreted exosomes.

2. The method of claim 1, wherein the extracellular vesicle mimetics have a membrane-bound protein, CD63.

3. The method of claim 1, wherein the extracellular vesicle mimetics increase levels of β-catenin, VRCN (Versican) and ALP in dermal papilla cells.

4. The method of claim 1, wherein the extracellular vesicle mimetics increases levels of phosphorylated AKT (pAKT) and phosphorylated ERK (pERK) in dermal papilla cells.

5. The method of claim 1, wherein the extracellular vesicle mimetics increase levels of Bcl-2 and PCNA in dermal papilla cells.

6. The method of claim 1, wherein the extracellular vesicle mimetics are absorbed into dermal papilla cells to promote cell proliferation.

7. The method of claim 1, wherein a drug for hair regeneration is loaded on the extracellular vesicle mimetics.

8. A method of regenerating hair, comprising:
preparing macrophage-derived extracellular vesicle mimetics by extruding macrophages sequentially using polycarbonate membrane filters of 10 µm, 5 µm and 1 µm, wherein the macrophage-derived extracellular vesicle mimetics have a size of 163 nm, the macrophage-derived extracellular vesicle mimetics comprising calnexin; and
administering a cosmetic composition comprising the macrophage-derived extracellular vesicle mimetics as an active ingredient to a subject,
wherein the macrophage-derived extracellular vesicle mimetics are not naturally secreted exosomes.

\* \* \* \* \*